(12) United States Patent
Mills et al.

(10) Patent No.: US 8,114,673 B2
(45) Date of Patent: Feb. 14, 2012

(54) SENSOR FOR OXIDISING AGENTS

(75) Inventors: Andrew Mills, Glasgow (GB); Soo-Keun Lee, Kyungpook (KR)

(73) Assignee: University of Strathclyde, Glasgow (GB)

(*) Notice: Subject to any disclaimer, the term of this patent is extended or adjusted under 35 U.S.C. 154(b) by 1528 days.

(21) Appl. No.: 10/487,761

(22) PCT Filed: Sep. 2, 2002

(86) PCT No.: PCT/GB02/03994
§ 371 (c)(1),
(2), (4) Date: Aug. 12, 2004

(87) PCT Pub. No.: WO03/021252
PCT Pub. Date: Mar. 13, 2003

(65) Prior Publication Data
US 2004/0258562 A1    Dec. 23, 2004

(30) Foreign Application Priority Data
Sep. 5, 2001 (GB) .................................. 0121444.4

(51) Int. Cl.
G01N 21/00 (2006.01)
G01N 22/00 (2006.01)
(52) U.S. Cl. ............... 436/77; 436/136; 422/57; 422/91
(58) Field of Classification Search .................... 422/57, 422/91; 436/136, 77
See application file for complete search history.

(56) References Cited

U.S. PATENT DOCUMENTS

| | | | |
|---|---|---|---|
| 4,169,811 A | 10/1979 | Yoshikawa et al. | |
| 4,526,752 A | 7/1985 | Perlman et al. | |
| 4,657,736 A | 4/1987 | Marsoner et al. | |
| 5,358,876 A * | 10/1994 | Inoue et al. ................... | 436/136 |
| 5,407,829 A | 4/1995 | Wolfbeis et al. | |
| 5,483,819 A | 1/1996 | Barmore et al. | |
| 5,583,047 A | 12/1996 | Blinka et al. | |

FOREIGN PATENT DOCUMENTS

| | | |
|---|---|---|
| GB | 2 132 348 | 4/1984 |
| JP | 54 005422 | 1/1979 |
| JP | 59 065764 | 4/1984 |
| JP | 62 012853 | 1/1987 |
| JP | 02 138866 | 5/1990 |
| JP | 2000 214155 | 8/2000 |
| WO | WO 95/29394 | 11/1995 |
| WO | PCT/GB00/02111 | * 12/2000 |

OTHER PUBLICATIONS

Doushita. Evaluation of Photocatalytic Activity by Dye Decomposition.(2001). Journal of Sol-Gel Science and Technology.22:91-98.*
International Search Report for PCT/GB02/03994 completed Nov. 12, 2002.

* cited by examiner

Primary Examiner — Krishnan S Menon
Assistant Examiner — Rebecca M Fritchman
(74) Attorney, Agent, or Firm — Alston & Bird LLP (57) ABSTRACT

This invention relates to an irreversible indicator for detecting oxidizing agents, or in particular an oxygen indicator, comprising at least one redox-sensitive dyestuff, at least one semiconductor material and at least one electron donor. This indicator is activated by exposure to light of about 200-400 nm. The invention also relates to UV light detector.

15 Claims, 8 Drawing Sheets

SENSOR FOR OXIDISING AGENTS

BACKGROUND OF THE INVENTION

This invention relates to an irreversible indicator for detecting oxidising agents, and in particular an oxygen indicator, comprising at least one redox-sensitive dyestuff, at least one semiconductor material and at least one electron donor. The indicator is activated by exposure to light of about 200-400 nm. The invention also relates to a UV light detector.

Modified atmosphere packaging (MAP) is widely used to prolong the useful life of many oxygen-sensitive items, such as: food, beverages, works of art, pharmaceuticals, medical diagnostic kits and sterilised packages. MAP includes: vacuum packaging, reduced oxygen packaging, oxygen absorption packaging and nitrogen and carbon dioxide flushed packaging. The major use of MAP is found in the food industry where it is routinely employed to extend the shelf life of: breads, cookies, cakes, pastries, nuts and snacks, candies and confectioneries, coffee and tea, whole fat dry foods, processed, smoked and cured meats and fish, cheeses and dairy products, dried fruits and vegetables, spices and seasonings, flour and grain items, fresh and pre-cooked pasta and noodles, birdseed and pet and animal food. It follows that a cheap, oxygen indicator is a highly desirable feature for any MAPed product, especially with regard to quality assurance and tamper-proofing. A number of indicators for this purpose have been reported previously. These indicators fall into two major categories: colourimetric and fluorimetric indicators.

Most colourimetric indicators for strong oxidising agents comprise a redox-sensitive dyestuff (such as methylene blue), an alkaline substance (such as calcium hydroxide) and a strong reducing agent (such as glucose) rendered strongly reducing by the alkaline substance. In the absence of strong oxidising agents the reducing agent reduces the usually highly coloured oxidised form of the redox-sensitive indicator to its reduced, usually much less coloured form. For example, the oxidised form of methylene blue (which is blue) is reduced, by alkaline glucose, to leuco-methylene blue (which is colourless). Leuco-methylene blue is readily oxidised back to methylene blue by a strong oxidising agent, such as oxygen. Such indicators need to be stored under anaerobic conditions and are usually reversible in response to oxidising agents and are light sensitive and have a responsivity that is markedly affected by the presence of acidic gases, such as $CO_2$ and $SO_2$.

Although the following now only refers to oxygen as the oxidising agent it should be appreciated that any oxidising agent is also applicable.

U.S. Pat. Nos. 4,169,811, 4,526,752, 5,358,876, 5,483,819 and 5,583,047 are relevant examples of the prior art of colourimetric oxygen sensors.

Most fluorimetric oxygen indicators comprise one or more indicating dyes that fluoresce strongly under anaerobic conditions, but have a much-reduced fluorescence under aerobic conditions. These indicators rely on the quenching of the electronically excited state of the indicator dye (such as the ruthenium (II) tris 4,7-dimethyl-(1,10-phenanthroline) complex) by oxygen. The fluorescent indicator dyes are usually encapsulated in an oxygen permeable matrix, such as a polymer. Most fluorimetric oxygen indicators are reversible in response to oxygen.

U.S. Pat. Nos. 4,657,736, 5,407,829, and UK patent application GB 2132348A are relevant examples of the prior art.

Current colourimetric oxygen indicators have a number of problems that have prevented their extensive application in MAP. These problems include one or more of the following: a relatively high cost, short shelf-life, a response that is affected by the presence of carbon dioxide (a common MAP packaging gas) and the need for anaerobic storage and, preferably, handling when being applied. Most fluorimetric oxygen indicators also suffer from a high relative cost and have the added problem of luminescence detection, since, in general the fluorescence from a fluorimetric oxygen indicator is less amenable to detection by the human eye than the colour change associated with a colourimetric oxygen indicator. Thus, with colourimetric oxygen indicators, untrained personnel can be used to judge if a package is still anaerobic, whereas with the fluorimetric oxygen indicators often a luminescence-detection system is required. Prior art devices and methods for oxygen detection also suffer from a lack of reliability and, because of their inherent reversibility towards oxygen, insufficient protection against deliberate tampering and compromise in food microbial safety.

As noted above both colourimetric and fluorimetric oxygen indicators usually give a reversible response towards oxygen. However, the latter is not a desirable feature in MAPed foods since, if the integrity of an oxygen-free MAPed food package is compromised, and air is let in, microbial growth can be so rapid that all the oxygen that leaks into the package is metabolized after a short time. This is particularly true if the air leak is small. Thus, following the creation of a small air leak in a MAPed package, within a short time a reversible colourimetric or fluorimetric oxygen indicator present in the package will indicate (correctly) the absence of oxygen, despite the compromise in the integrity of the package with its concomitant deleterious effect on food safety (i.e. undesirable microbial growth).

It is an object of the present invention to obviate/mitigate at least one of the aforementioned problems.

SUMMARY OF INVENTION

According to a first aspect of the present invention there is provided an indicator for detecting oxidising agents comprising:
- at least one redox sensitive material which displays different visible properties in the oxidised and reduced forms;
- at least one electron donor; and
- at least one semiconductor material specifically sensitive to light of about 200-400 nm, and wherein upon irradiation of said semiconductor material by light of about 200-400 nm an electron is donated by the electron donor to the semiconductor material which in turn provides an electron to the redox sensitive material causing the redox sensitive material to become reduced.

By specifically sensitive to light of about 200-400 nm (ie. UV light) is meant that the oxidising agent indicator is substantially insensitive to light outwith that of about 200-400 nm.

Thus, in the 'light-activation' step the semiconductor material becomes electronically excited, i.e. activated under UV irradiation. The electronically excited state of the semiconductor material is a better oxidising agent than its non-excited, ground-state, form. As a consequence the excited semiconductor material is able to oxidize the electron donor present in the indicator formulation. The electron donor is chosen so that this process is irreversible, i.e. the electron donor is sacrificed. The key products of the above photoinduced electron transfer reaction are the irreversibly oxidised form of the sacrificial electron donor and the reduced form of the semiconductor material. Under anaerobic conditions the latter then reduces the redox-sensitive material to its highly-coloured, oxygen-insensitive form to its less-coloured, oxygen-sensitive form. The semiconductor material is also able to store, or pool, reduction potential on its surface and/or reduce other species present so that they can act as an electron pool to reduce the redox-sensitive material. The 'depth' of this electron pool will depend directly upon the duration of the irradiation; the longer the deeper. The overall 'light activation' process enables the semiconductor material to return to its original state, ready to absorb another photon of light and begin the process of electron transfer from the electron donor to the redox-sensitive material again. As a consequence, the semiconductor material is usually referred to as a photocatalyst, or photosensitiser, i.e. a material that absorbs light and then effects a change but, is itself left unchanged at the end of the process.

The above describes in general terms the principles behind the light-activation step that turns the redox indicator present in the indicator formulation from its initial usually coloured (and/or non-fluorescent) form to its reduced (usually non-coloured and/or fluorescent) form. The latter is sensitive towards most strong oxidising species, including oxidising gases such as $O_2$, $NO_2$ and $O_3$. Thus, exposure of the 'light-activated' system to a strongly oxidising species causes the redox indicator to change from its reduced (usually non-coloured and/or fluorescent) form to its oxidised (usually highly coloured and/or non-fluorescent form). This latter step is the 'responding to strong-oxidising agents' or regeneration step and in the indicator formulation it results in a clear optical (coloured and/or fluorescent) change in the indicator formulation.

Usually the oxidising agent is gaseous. Typically, the oxidising agent is oxygen and the indicator is therefore an oxygen indicator.

For the necessary reactions and the colour and/or fluorimetric change to occur the redox sensitive material and the components of the indicator must be brought into intimate contact. Thus, the indicator may be in the form of a tablet or pellet in which the components are, for example, pressed together, or as a plastic film in which the components are encapsulated in some medium, such as a polymer. Alternatively, the indicator may be in the form of an ink which may form a label, LOGO or text i.e. writing.

The intimate contact of the various components of the indicator allows the redox sensitive material to undergo a redox reaction wherein there is a transfer of electrons from the photogenerated reduced form of the semiconductor material to the redox sensitive material.

Typically, the redox sensitive material may be a dye such as a thiazine dyestuff, an oxazine dyestuff, an azine dyestuff, a triphenylmethane dyestuff, an indophenol dyestuff, an indigo dyestuff, viologen and/or mixtures thereof.

The electron donor has the ability to donate electrons, preferably irreversibly. Typically, the electron donor is a mild reducing agent. The electron donor may, for example, be an amine (e.g. NaEDTA and TEOA), reducing saccharide (such as glucose and fructose), readily oxidisable polymer (such as polyvinyl alcohol), and other general anti-oxidant (such as ascorbic and citric acid) or easily oxidizable material (such as glycerin) and/or mixtures thereof.

The semiconductor material has the ability to form an excited electronic state that is sufficiently oxidising to oxidize the sacrificial electron donor and has a reduced form that is able to reduce the redox sensitive material.

By semiconductor material is meant materials which are usually solids which have an electronic structure comprising a nearly filled valence band and a nearly empty conductance band. The difference in energy between these two levels is called the bandgap of the semiconductor. A semiconductor material has a bandgap that typically lies in the range of 0.1-4 eV and exhibits a degree of conductivity that is usually less than that of metals which have bandgaps less than 0.1 eV but greater that that of insulators which have bandgaps greater than 4 eV. The conductivity of the semiconductor material increases with increasing temperature. The semiconductor material may be classed as a photosensitiser or a photocatalyst i.e. a material that is able to promote a process through the creation of an electronically exited state generated by the absorption of a photon of light. The energy of the light is usually greater than or equal to the bandgap. The initial excitation of the system is followed by subsequent electron transfer and/or energy transfer which results in overall photsensitised or photocatalysed reactions. In a photosensitised or photocatalysed reaction the photocatalyst or photosensitiser remains chemically unchanged at the end of the overall reaction.

The semiconductor material may bean oxide of titanium (such as titanium (IV) oxide; $TiO_2$, and strontium tiatanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof.

The indicator may further comprise a binder which binds all the components together. The binder may be a polymeric material such as gelatin, hydroxyethyl cellulose (HEC), polyvinyl alcohol (PVA), ethyl cellulose (EC), cellulose acetate (CEA), polypyrolidone (PVP), polyethylene oxide, and polymethylmethacrylate (PMMA).

The indicator may be supported on at least one inert material, such as glass, paper, fabric, ceramic and metal.

The indicator may be in the form of an ink and printed on a substrate.

Typically, the indicator is, in its non-activated form, stable over many months under ambient atmospheric conditions. A typical indicator will continue to work as an oxygen sensor for over 1 year when stored under ambient conditions in the dark.

According to a second aspect of the present invention there is provided a method of detecting oxidising agents, comprising the steps of; providing an oxidising agent indicator comprising:
at least one redox sensitive material which displays different visible properties in the oxidised and reduced forms;
at least one electron donor; and
at least one semiconductor material specifically sensitive to light of about 200-400 nm, and
activating the oxidising agent indicator by irradiating with light of about 200-400 nm so as to convert the redox material into its reduced form which is stable under non-oxidising conditions, and exposing the indicator to an oxidising agent whereupon the redox material is oxidised resulting in a visible change of the indicator.

By specifically sensitive to light of about 200-400 nm (ie. UV light) is meant that the oxidising agent indicator is substantially insensitive to light outwith that of about 200-400 nm.

Typically, the oxidising agent to be detected is oxygen.

In particular, near UV light (i.e. 300-400 nm) is used.

Conveniently, the activated oxidising agent indicator once exposed to an oxidising agent changes colour and/or fluorescence. Desirably, the change in colour, and/or fluorescence, should be irreversible and persists indefinitely under either oxidising or non-oxidising conditions (provided the indicator is not exposed to another burst of UV light) i.e. the colour, and/or fluorescence, change cannot be reversed simply by changing the atmosphere from oxidising to non-oxidising.

Typically, the kinetics of the light activation step are insensitive towards the level of water or carbon dioxide or nitrogen in the ambient atmosphere.

Conveniently, the kinetics of the reaction between the reduced redox-sensitive material and oxidising agent are insensitive towards the level of water or carbon dioxide or nitrogen in the ambient atmosphere.

According to a third aspect of the present invention there is provided a modified atmosphere package comprising an oxidising agent indicator comprising:

at least one redox sensitive material which displays different visible properties in the oxidised and reduced forms;

at least one electron donor; and at least one semiconductor material specifically sensitive to light, of about 200-400 nm wherein upon irradiation of light of about 200-400 nm an electron is donated by the electron donor to the semiconductor material which in turn provides an electron to the redox sensitive material causing the redox sensitive material to become reduced which displays different visible properties in the oxidised and reduced forms.

By specifically sensitive to light of about 200-400 nm (ie. UV light) is meant that the oxidising agent indicator is substantially insensitive to light outwith that of about 200-400 nm.

Typically, the oxidising agent is oxygen and the indicator is therefore an oxygen indicator.

Conveniently, the light used is near UV light (i.e. 300-400 nm).

Typically, the modified atmosphere packaging comprises food, beverages, works of art, pharmaceuticals, medical diagnostic kits and sterilised packages.

According to a fourth aspect of the present invention there is provided a method of detecting oxidising agents in modified atmosphere packaging using an oxidising agent indicator comprising:

at least one redox sensitive material which displays different visible properties in the oxidised and reduced forms;

at least one electron donor; and at least one semiconductor material specifically sensitive to light of about 200-400 nm, the indicator is activated by irradiating with light of about 200-400 nm so as to convert the redox material into its reduced form which is stable under non-oxidising conditions, until such time as the indicator is exposed to an oxidising agent whereupon the redox material is oxidised resulting in a visible change in the indicator.

By specifically sensitive to light of about 200-400 nm (i.e. UV) light is meant that the oxidising agent indicator is substantially insensitive to light outwith that of about 200-400 nm.

Typically, the oxidising agent is oxygen and the indicator is therefore an oxygen indicator.

Conveniently, the light used is near UV light (i.e. 300-400 nm).

Typically, the modified atmosphere packaging comprises food, beverages, works of art, pharmaceuticals, medical diagnostic kits and sterilised packages.

According to a fifth aspect of the present invention there is provided a detector for indicating exposure to light of about 200-400 nm comprising an oxidising agent indicator comprising:

at least one redox sensitive material which displays different visible properties in the oxidised and reduced forms;

at least one electron donor; and at least one semiconductor material specifically sensitive to light of about 200-400 nm, capable of being activated upon irradiation of light of about 200-400 nm wherein a colour change indicates exposure to light of about 200-400 nm.

By specifically sensitive to light of about 200-400 nm (i.e. UV light) is meant that the UV indicator is substantially insensitive to light outwith that of about 200-400 nm.

The more UV light the greater the amount of colour change.

The colour change is a progressive change and therefore may form a graduated scale to indicate how much UV light the indicator has been exposed to.

The indicator may incorporate, or have a cover of, a polymer with a very low oxidising agent permeability, such as PET, EVOH, PVDC or regenerated cellulose (as found in Sellotape (Registered Trade Mark)) which has the effect of largely preventing the colour change of the UV-light activated indicator upon exposure to an oxidising agent, such as oxygen. Such an indicator film will be very insensitive to the presence of an oxidising agent, such as oxygen. As a result, in the absence and/or presence of the oxidising agent the indicator will provide a measure of how much UV light it has been exposed to, since the degree of bleaching it undergoes (upon exposure to UV light) will be related to the total amount of UV light incident on the indicator. Thus, a measure of UV light is provided by an assessment of the extent of the initial colour change undergone by the indicator upon exposure to the UV light.

The detector may also be used to determine how long a package, with its contents originally stored in the absence of oxygen, has been opened. In this situation, exposure of the indicating film to UV light, in the absence of the oxidising agent, the indicator in the indicator film will be converted, from its usually highly coloured oxidized form, into its reduced, usually colourless and oxygen sensitive form. The indicator film will remain in this bleached, i.e. reduced, form for as long as the indicator film remains in an environment that is free of oxidizing agent, such as oxygen. However, upon exposure to an oxidising agent, such as oxygen or air, the rate at which the indicator in the oxidising agent indicator film transforms from its reduced (usually bleached) form to its oxidized, usually highly coloured form, will depend upon the permeability of the polymer material towards the oxidizing agent; the more impermeable and thicker the slower the response. Use of polymers of low oxygen permeability, such as PET, PVDC and EVOH, and reasonable thickness (typically 5-300 microns) allow indicator films to be made that change colour over a period of days, hours or weeks. As a consequence, through judicious choice of polymer and polymer thickness, either as an encapsulating material or as a cover for the indicator film, or array of films that indicate(s), via the extent of any colour change, how long the film (and or package contents) has been exposed to the oxidizing agent, following its initial activation with UV light. Such an indicator could, therefore, be used to indicate how long a MAPed package had been opened for.

According to a sixth aspect of the present invention there is provided a method for indicating exposure to light of about 200-400 nm using an oxidising agent indicator comprising:

at least one redox sensitive material which displays different visible properties in the oxidised and reduced forms;

at least one electron donor; and at least one semiconductor material specifically sensitive to light of about 200-400 nm, wherein a colour change in the indicator indicates exposure to light of about 200-400 nm.

By specifically sensitive to light of about 200-400 nm (ie. UV light) is meant that the oxidising agent which acts as a UV sensor is substantially insensitive to light outwith that of about 200-400 nm.

The indicator may incorporate, or have a cover of, a polymer with a very low oxidising agent permeability, such as PET, EVOH, PVDC or regenerated cellulose (as found in Sellotape (Registered Trade Mark)) which has the effect of largely preventing the colour change of the UV-light activated indicator upon exposure to an oxidising agent, such as oxygen. Such an indicator film will be very insensitive to the presence of an oxidising agent, such as oxygen. As a result, in the absence and/or presence of the oxidising agent the indicator will provide a measure of how much UV light it has been exposed to, since the degree of bleaching it undergoes (upon exposure to UV light) will be related to the total amount of UV light incident on the indicator. Thus, a measure of UV light is provided by an assessment of the extent of the initial colour change undergone by the indicator upon exposure to the UV light.

The indicator may also provide a method of determining how long a package, with its contents originally stored in the absence of an oxidising agent has been exposed to the oxidising agent. For example, an indicator film will exhibit an increasing sensitivity towards any oxidising agent present, such as oxygen, with decreasing polymer oxidising agent permeability. As a consequence, through judicious choice of polymer and polymer thickness, either as an encapsulating material or as a cover for the indicator film, or array of films, that indicate(s), via the extent of any colour change, how long the film (and or package contents) has been exposed to the oxidising agent, following its initial activation with UV light. Such an indicator could, therefore, be used to indicate how long a MAPed package had been opened for.

BRIEF DESCRIPTION OF THE DRAWINGS

Embodiments of the present invention will now be described, by way of example only, with reference to the accompanying drawings in which.

DETAILED DESCRIPTION OF THE INVENTION

Most colourimetric oxygen indicators rely on a reaction between a redox-sensitive indicator dye, such as methylene blue, and a strong reducing agent, such as glucose in a strongly alkaline (pH>12) environment. This reaction leads to the reduction of the redox-sensitive dye and concomitant colour change. The redox dye is readily reoxidised back to its original colour upon exposure to oxygen.

Although the following discussion is limited to that of oxygen it should be realised that the discussion is applicable to any other types of oxidising agents.

The novel oxygen indicator described utilises at least one redox-sensitive dye (eg. a thiazine dyestuff, oxazine dyestuff, azine dyestuff, indophenol dyestuff, indigo dyestuff, viologen or a mixture thereof). The redox-sensitive dye is chosen so that, at the levels employed in the oxygen indicator, it has little or no absorbance in the near UV, i.e. 300-400 nm. The redox-sensitive dyestuff is also chosen so that its reduced form has a different colour, and/or fluorescence, to its oxidised form and is oxidised to the latter by oxygen. The oxygen indicator utilises a sacrificial electron donor (SED), which is a mild reducing agent, such as triethanolamine (TEOA) and the disodium salt of ethylenediammine tetraacetic acid (NaEDTA). The mild reducing agent is selected on the basis that, at the levels employed in the oxygen indicator, it: (a) does not reduce the redox-sensitive dye at a significant rate under either aerobic or anaerobic conditions and (b) it does not reductively quench the electronically excited state of the redox-sensitive dye under either aerobic or anaerobic conditions. These conditions being satisfied, the combination of redox-sensitive dye and mild reducing agent is stable and long-lived under ambient atmospheric and typical room-light conditions. Note that no strong alkaline material is present in the oxygen indicator since the latter turns many mild reducing agents, such as reducing sugars, TEOA and NaEDTA into strong reducing agents and conditions (a) and (b) would no longer be satisfied.

Figure 1:
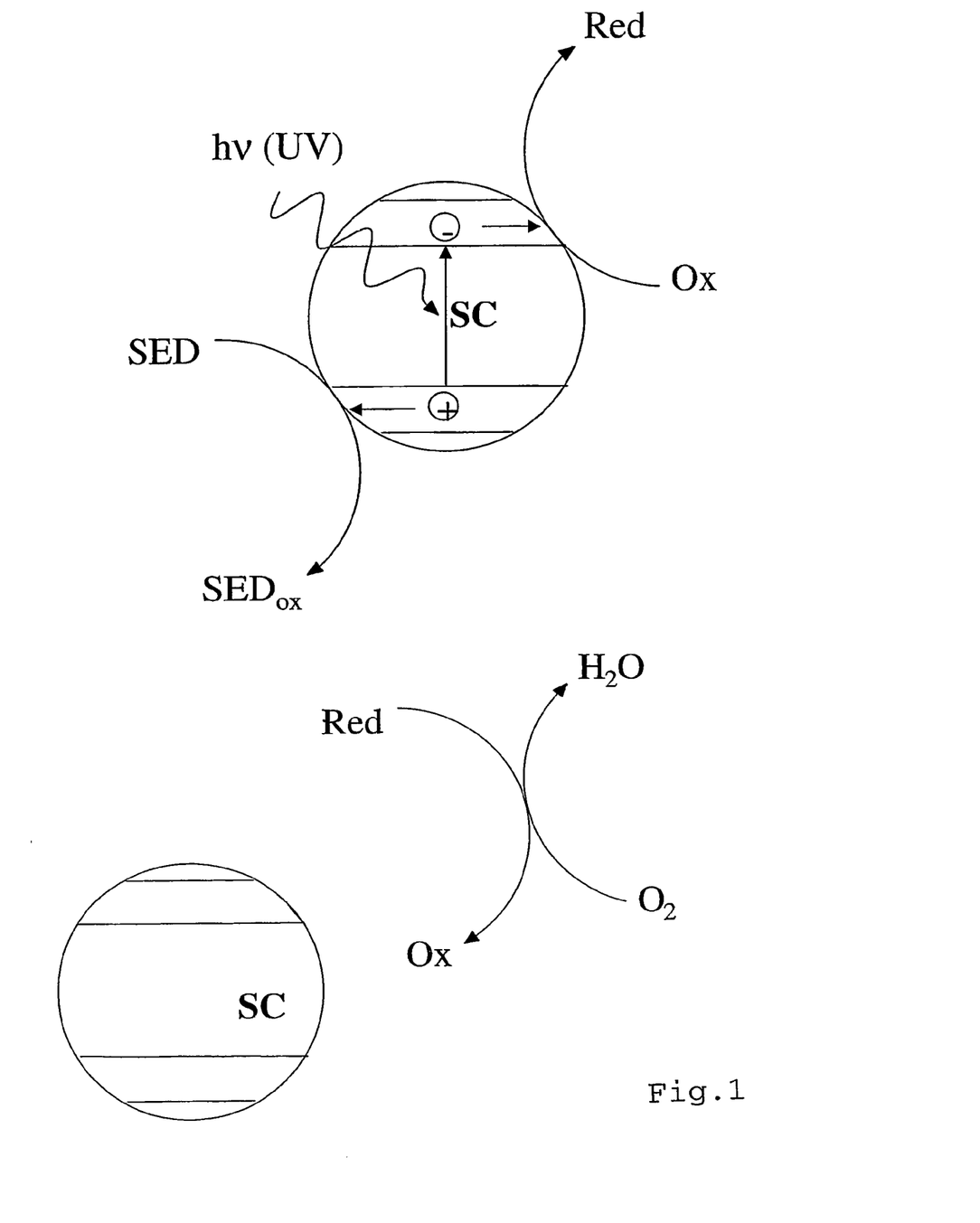
FIG. 1 is a schematic illustration of the two step mechanism of irreversible oxygen detection an oxygen indicator according to the present invention.

A near UV-absorbing semiconductor photoactive material (SC) is also present in the oxygen indicator. The role of the semiconductor is to initiate the process of indicator activation by absorbing some of the burst of near UV light that the indicator is exposed to. Absorption of a photon of near UV light by the semiconductor material (in particle, film (micro or nanocrystalline) or single crystal form leads to the creation of a photogenerated electron-hole pair. The semiconductor material is selected so that the photogenerated electron is sufficiently reducing in power that it can reduce the redox-sensitive dye present and the hole is sufficiently oxidising that it can oxidise the mild reducing agent present. The net effect upon UV activation of the combination of semiconductor material/redox-sensitive dye/sacrificial electron donor that goes to make the oxygen indicator is that the dye is converted to its differently coloured, or fluorescent, reduced, oxygen-sensitive, form, eg. methylene blue (which is blue) is reduced to leuco-methylene blue (which is colourless) and the sacrificial electron donor, or mild reducing agent, is oxidised, i.e. SED to $SED_{ox}$; both latter species are usually colourless. A schematic illustration of this near UV light activation step is illustrated in part (a) of FIG. 1. If the near UV light activation step is carried out and maintained under anaerobic conditions the reduced dye, Red, is stable and lives indefinitely. However, any subsequent change in the ambient atmosphere from anaerobic to aerobic results in the reduced form of the dye, Red, being oxidised by oxygen back to its original form, Ox. A schematic illustration of this second oxygen sensitive step is illustrated in part (b) of FIG. 1.

Figure 2:
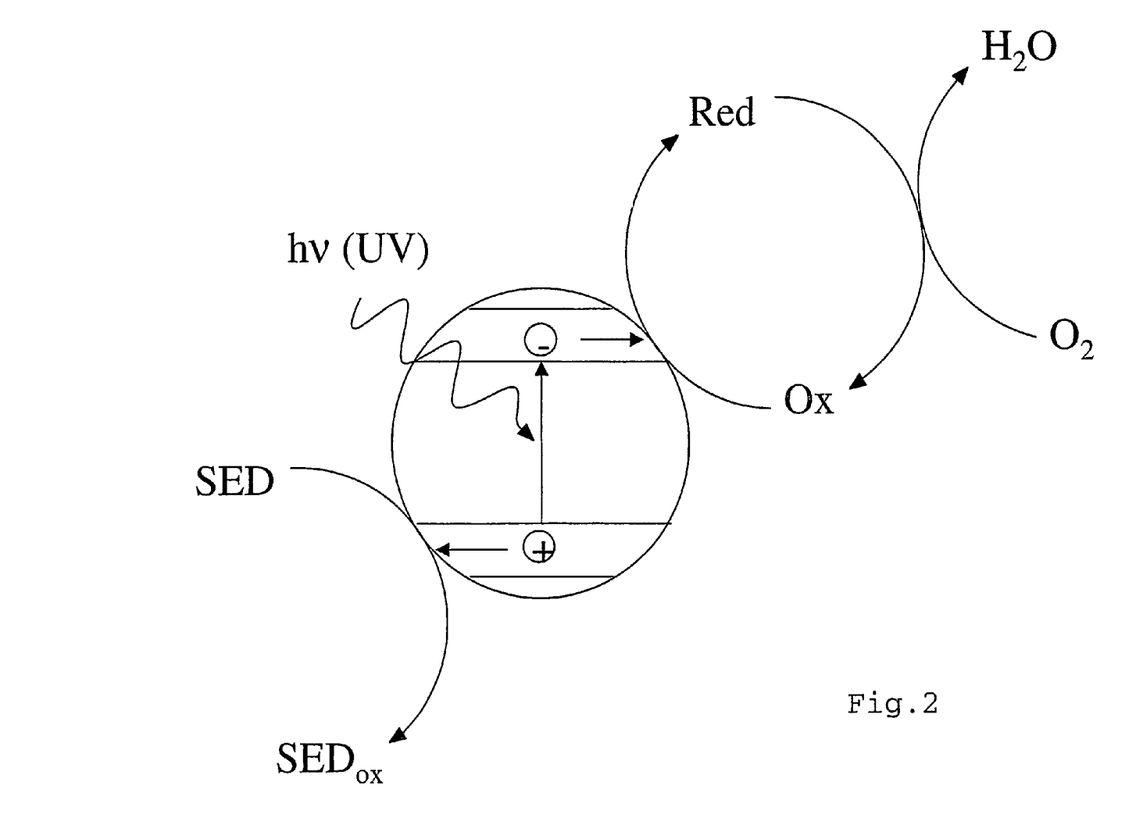
FIG. 2 is an overall reaction scheme for the oxygen indicator.

A schematic illustration of the overall process is illustrated in FIG. 2. The overall scheme can also be represented by the following series of reaction equations:

Light Activation Step (Under Anaerobic Conditions):
Absorption $$SC+h\nu \rightarrow SC(e^-;h^+)$$

Where hv represents the energy of an absorbed photon; the latter will have an energy greater than or equal to the bandgap energy of the semiconductor (SC), i.e. an ultra-bandgap photon. For the present invention the most favoured semiconductors will have large bandgaps (3-4 eV) and so will require excitation by near UV light. $SC(e^-;h^+)$ represents an electronically excited form of the semiconductor, SC, and will have a photogenerated electron, $SC(e^-)$, and a photogenerated hole, $SC(h^+)$ available for reaction.

Scavenging of the Photogenerated Electron $$SC(e^-;h^+)+Ox \rightarrow Red+SC(h^+)$$

Where Ox is the aerobically (and anaerobically) stable, coloured form of the redox sensitive dye and Red is the reduced form of Ox which not only is markedly different in colour, and/or fluorescence, to Ox but also reacts readily with oxygen and, consequently, is only stable under anaerobic conditions.

Scavenging of the Photogenerated Hole $$SC(h^+)+SED \rightarrow SC+SED^+$$

The mild reducing agent, SED, is chosen so that it does not react directly with Ox, as is the case for most other colourimetric oxygen indicators, and so that it preferably reacts irreversibly with the photogenerated hole.

Oxygen Indicating Step

The reduced form of the redox sensitive dye is stable under anaerobic conditions. However, upon exposure to oxygen the following reaction takes place:

$$Red+O_2 \rightarrow Ox+H_2O$$

i.e. the original (i.e. that seen before light activation) colour, and/or fluorescence, of the indicator is returned, thus indicating the presence of oxygen.

Figure 7:
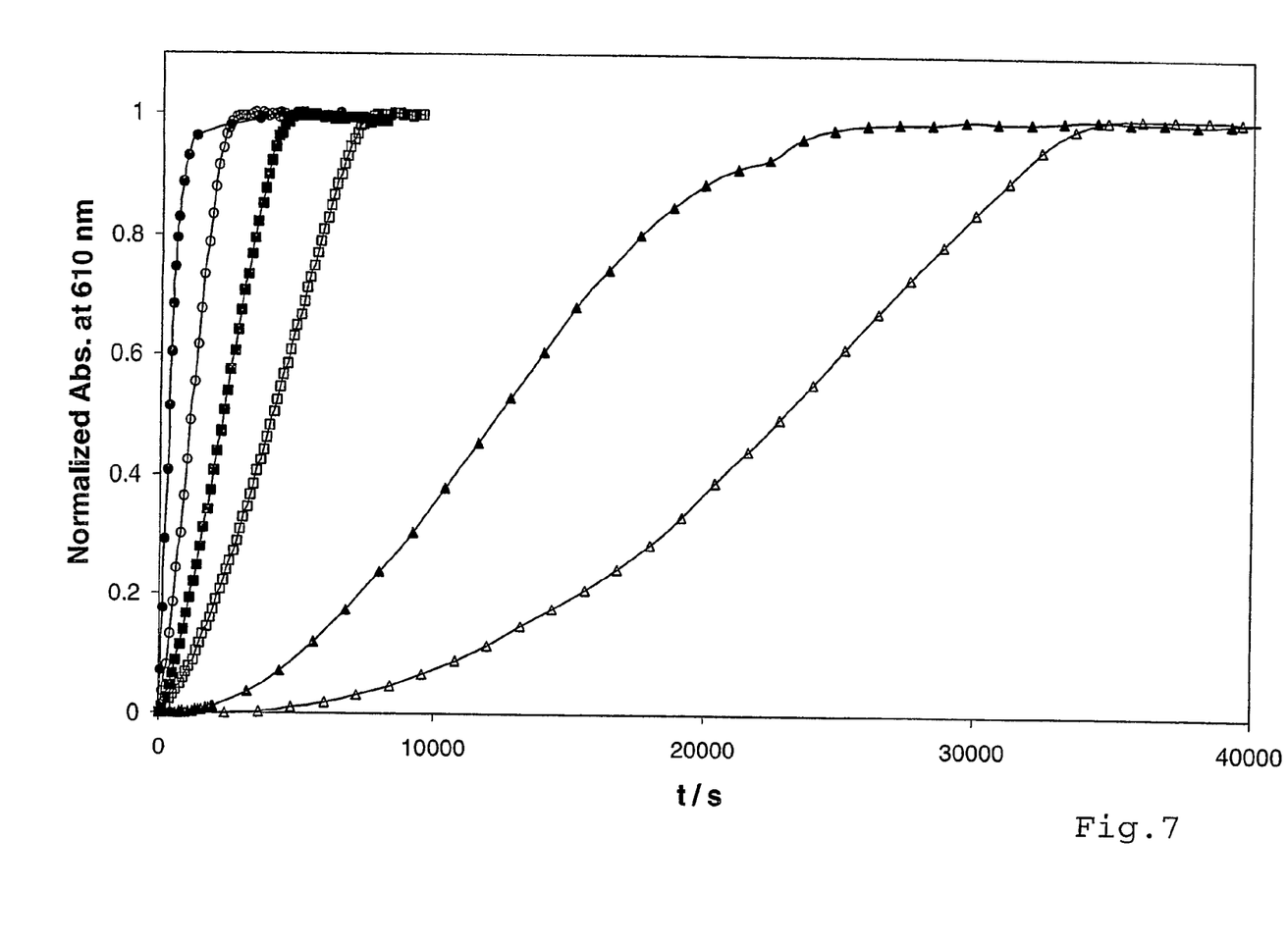
FIG. 7 relates to recovery curves of a typical oxygen indicator film comprising methylene blue, titanium dioxide and triethanolamine encapsulated in hydroxyethyl cellulose and covered with films of the oxygen-impermeable polymer PET of increasing thickness (from left to right; 0, 15, 35, 60, 130, and 230 microns, respectively)

FIG. 7 relates to the observed variation in the absorbance at 610 nm of a typical oxygen indicator film comprising methylene blue, titanium dioxide and the sacrificial electron donor (SED) triethanolamine, encapsulated in the polymer hydroxyethyl cellulose. In FIG. 7 each of the indicator films is covered by different thicknesses of polyethylene terephthalate (PET) polymer (a polymer with a low oxygen permeability) of different thicknesses ranging from about 0 to 230 microns. As the thickness of the PET covering layer is increased, the recovery of the blue colour of the sensor films (that have already been pre-irradiated with UV light and, therefore, have been photobleached/oxygen activated) decreases significantly.

Figure 8:
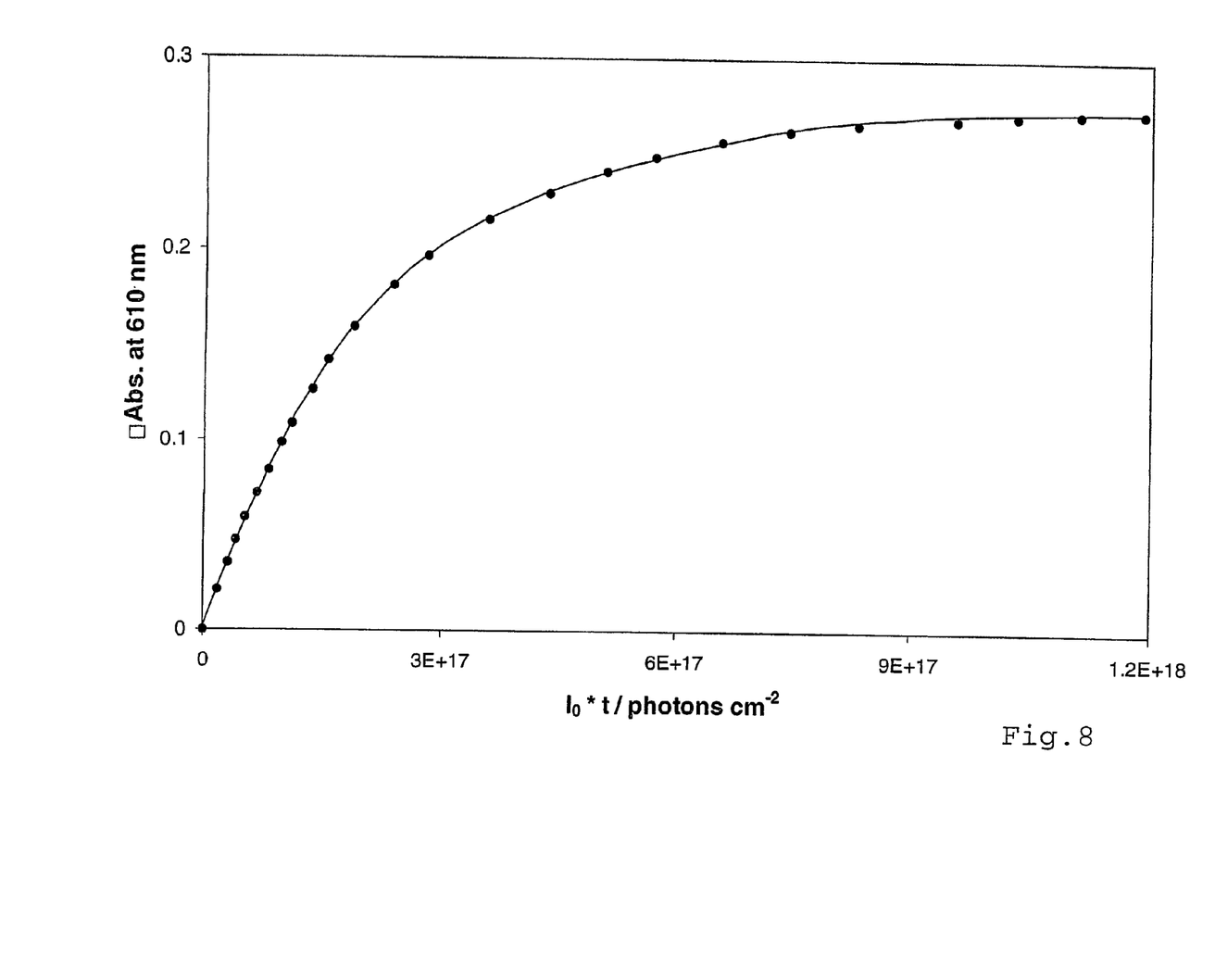
FIG. 8 relates to observed changes in absorbance of an indicator comprising methyethelene blue, titanium dioxide and triethanolamine encapsulated in hydroxyethyl cellulose and covered with a layer of Sellotape (Registered Trade Mark), as a function of total number of UV photons absorbed by the indicator film.

FIG. 8 relates to the observed change in absorbance at 610 nm of a typical indicator film comprising methyethelene blue, titanium dioxide and the sacrificial electron donor (SED) triethanolamine encapsulated in the polymer hydroxyethyl cellulose. In this embodiment the typical film is covered with a largely oxygen impermeable film, in this case Sellotape (Trade Mark) and the measured changes in absorbance, illustrated in FIG. 8, are those recorded when the film was exposed to the same UV light intensity, but for different times, and/or the same time of exposure at UV light, but of different intensities. Thus, FIG. 8 represents a calibration graph for the Sellotape (Trade Mark) covered indicator which allows the measurement of the level of ambient UV light.

The rate of reaction between the reduced form of the redox dye, Red, and oxygen may be rendered mass-transfer dependent, by making the rate of diffusion of oxygen from the ambient air through the film the rate determining step. The latter can be achieved by making the diffusion process very slow through the use of polymers with low oxygen permeabilities such as polyethylene terephthalate, either as the polymer encapsulating medium or as a film covering the film indicator. Through the use of such a diffusion barrier it is possible to create a type of indicator film that (after photobleaching by UV light) exhibits a recovery time (when exposed to air) that depends upon the thickness of the diffusion barrier film; the thicker the oxygen barrier, the slower the film recovery. When used as an oxygen indicator, in an oxygen-free package, the colour recovery times of this type of indicator can be made sufficiently long, i.e. hours and/or days, that it can provide an indication of how long a modified atmosphere package has been opened, after it is opened and air allowed in. Typical results for such an indicator are illustrated in FIG. 7. If a very oxygen impermeable membrane is used as the barrier, the indicator is no longer sensitive towards oxygen and the degree of bleaching the film undergoes upon exposure to UV light can be used as a measure of the level of ambient UV light the film has been exposed to, i.e. such an indicator is a UV-light level indicator. The results recorded for a film operating in this mode are illustrated in FIG. 8.

The oxygen indicator can be re-used simply by reactivating with ultra-bandgap light, the preferred wavelength range of which falls in the near UV. Note that the oxygen indicator is not selective towards oxygen, but will also respond to most strong oxidising agents if they are present, such as chlorine, nitrogen dioxide and ozone. This lack of selectivity towards oxygen is also a feature of almost all other oxygen indicators. Fortunately, in most packages (especially food) and the ambient environment, there are no, or very little, oxidising agents other than oxygen. The sensitivity of the oxygen indicator towards oxidising gases other than oxygen may be exploited to create indicators for these other gases.

The oxygen sensing action of the oxygen indicator is irreversible in that it only works after it has been activated by exposure to a burst of near UV light. Once reoxidised by oxygen it cannot be reactivated unless deliberately exposed to another burst of near UV light. Typical ambient room light does not possess sufficient UV light to drive this light activation process at a significant rate. Although prolonged exposure to sunlight can drive the light activation step forward, most packaged goods, including food, also suffer unwanted deleterious effects if exposed to bright sunlight. As a consequence, under the typical lighting conditions employed in handling most MAPed goods, the oxygen indicator will not be activated.

The redox-sensitive dyestuff makes the colour, and/or fluorescence, change associated with the oxygen indicator that occurs between conditions when oxygen is present and conditions where it is absent. This colour, and/or fluorescence, change is unaffected by the presence of the sacrificial electron donor, semiconductor material and polymer binder. This colour, and/or fluorescence, change is also unaffected by the level of water or carbon dioxide (a popular MAP packaging gas) present in the atmosphere surrounding the oxygen indicator. That is the dyestuffs, upon photoreduction by the near-UV, light-absorbing semiconductor, become colourless or another colour, and/or change in fluorescence, in the substantial absence of oxygen. The dyestuffs include: thiazine dyestuffs (such as: methylene blue, thionin and toluidine blue), oxazine dyestuffs (such as: resazurin, safranine O, and celestine blue), azine dyestuffs, (such as: and cresyl violet acetate and azure A), indophenol dyestuffs (such as dichloroindophenol), indigo dyestuffs (such as; indigo and Indigo carmine), viologens (such as heptyl and benzyl viologen) and mixtures thereof.

The semiconductor material drives the reduction of the redox-sensitive dye by the sacrificial electron donor, upon absorption of some of the burst of near UV light used to activate, i.e. make sensitive towards oxygen, the oxygen indicator. The semiconductor material may be used in various forms, including: as micro and nanocrystalline powder particles dispersed in a polymer encapsulating material or pressed in the form of a tablet or pellet, or as a micro or nanocrystalline film. The semiconductor material is usually biologically and chemically inactive, unless irradiated with light of energy greater than or equal to its bandgap. Ideally, the bandgap of the semiconductor should fall in the near UV region, i.e. 3.1 to 4.1 eV (i.e. 400 to 300 nm). Typically the semiconductor should be selected from a group that includes the oxides of titanium (such as titanium (IV) oxide; $TiO_2$, and strontium tiatanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof. The sacrificial electron acceptor is any species that reacts readily with the photogenerated hole on the semiconductor but does not react directly or significantly with either the redox-sensitive dye (under aerobic or anaerobic conditions) or with oxygen (under aerobic conditions). Examples of such a sacrificial electron donor can be found amongst the following categories: amines (such as NaEDTA and TEOA), reducing saccharides (such as glucose and fructose), readily oxidisable polymers (such as polyvinyl alcohol), and other general antioxidants (such as ascorbic and citric acid) and mixture thereof. Although some of the above are sometimes cited as examples of strong reducing agents (such as glucose and TEOA), this is only the case if a strong alkali is also present. In the present invention no strong alkali is used and all sacrificial electron donors cited above are as a consequence only mildly reducing.

The polymer is a binder that helps hold all the other components of the oxygen indicator together in intimate contact. Ideally the polymer should be chemically and biologically inert, soluble in a common, easy to handle solvent, colourless, largely transparent to near UV light and compatible with all the other oxygen indicator components. Examples of such polymers include: gelatin, hydroxyethyl cellulose (HEC), polyvinyl alcohol (PVA), ethyl cellulose (EC), cellulose acetate (CEA), polypyrolidone (PVP), polyethylene oxide and polymethylmethacrylate (PMMA).

When combined with a suitable solvent, the initial form of the oxygen indicator is as an ink or castable solution that can be printed or cast on a wide variety of supports. Examples of typical solvents that can be used include: water, alcohols (such as ethanol and methanol), ketones (such as acetone), alkylhalides (such as chloromethane) and aromatics (such as toluene).

EXAMPLES

The present invention is further illustrated by the following non-limiting examples. A shorthand summary of the composition of each example of an oxygen indicator will be referred to in the form:

redox-sensitive dye/sacrificial electron donor/semiconductor/polymer

Unless stated otherwise, in all the examples cited the oxygen indicator composition (or ink) was cast on 22 mm diameter glass cover slips, i.e. the supporting substrate was glass. The casting process usually involved placing 2-3 drops (ca. 0.1 ml) of the ink on a glass cover slip and spreading the solution evenly. For each indicator, the glass disc with its spread oxygen indicator composition was then spun at 6000 rpm for 30 s using a spin coater. After this process, the final film was dry and ready for use. Such films could be stored under ambient atmospheric conditions, away from direct sunlight, for over a year with little sign of deterioration.

Example 1

$MB/TEOA/TiO_2/HEC$

Figure 3:
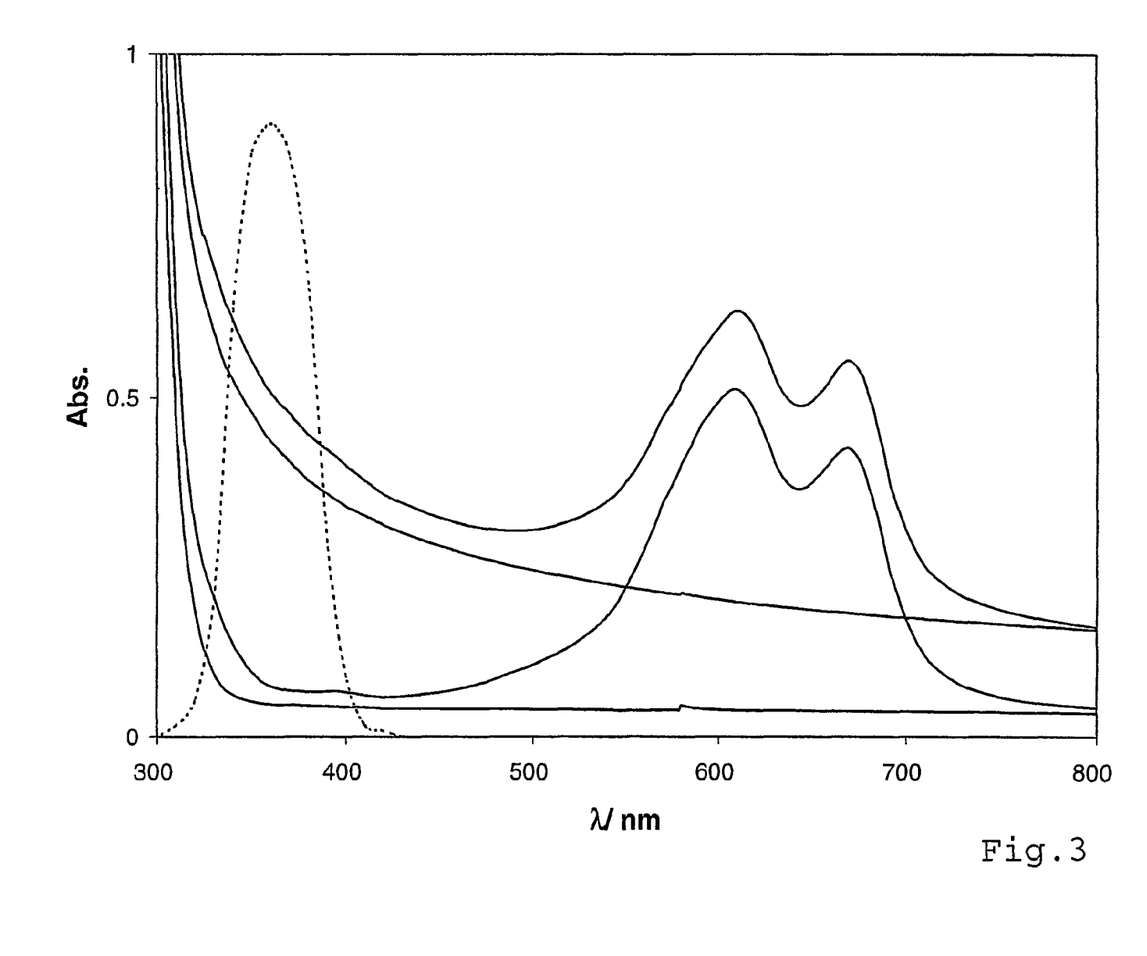
FIG. 3 is a UV/Visible spectra of a glass cover slip coated with methylene blue in hydroxyethyl cellulose, $TiO_2$ in hydroxyethyl cellulose and methylene blue and $TiO_2$ and hydroxyethyl cellulose.

A typical film was prepared as follows: 5 g of a 5 wt % aqueous dispersion of titanium (IV) oxide, i.e. $TiO_2$ (Degussa P25), 1 g of a 5 wt % aqueous solution methylene blue (MB) and 0.3 g of triethanolamine were mixed with 20 g of a 5 wt % aqueous solution of hydroxyethyl cellulose (HEC) using a magnetic stirrer (30 min). This oxygen indicator ink was then cast onto a glass cover slip as described above. The key UV/visible spectrophotometric features of the final oxygen indicator are illustrated in FIG. 3. The UV/Visible absorption spectrum (solid line; bottom spectrum in FIG. 3) shows that the supporting substrate used in Example 1 does not absorb appreciably UV/Visible light at wavelengths>310 nm. The UV/Visible spectrum of the redox-sensitive dye (MB) alone encapsulated in the HEC polymer is also illustrated in FIG. 3 (solid line, second from bottom spectrum) and shows that the dye has little or no absorbance in the near UV (i.e. from 300-400 nm). It also follows that HEC does not absorb appreciably in this spectral region. In contrast, $TiO_2$ (dispersed in HEC) does strongly absorb in this region, as illustrated in FIG. 3 (second from top spectrum; solid line). The overall UV/Visible absorption spectrum of oxygen indicator Example 1 is also illustrated in FIG. 3 (top solid line) and shows that the absorbances of the various components are additive and that, as a consequence, the major absorption in the near UV region is due to the presence of the $TiO_2$ semiconductor. The broken line illustrated in FIG. 3 is the spectral profile of a typical near-UV lamp, i.e. a blacklight lamp. These results show that for the oxygen indicator Example 1, the major species that absorbs near UV light is the semiconductor, $TiO_2$ and that it can be easily activated using light from a common blacklight lamp, i.e. near-UV light.

Figure 4:
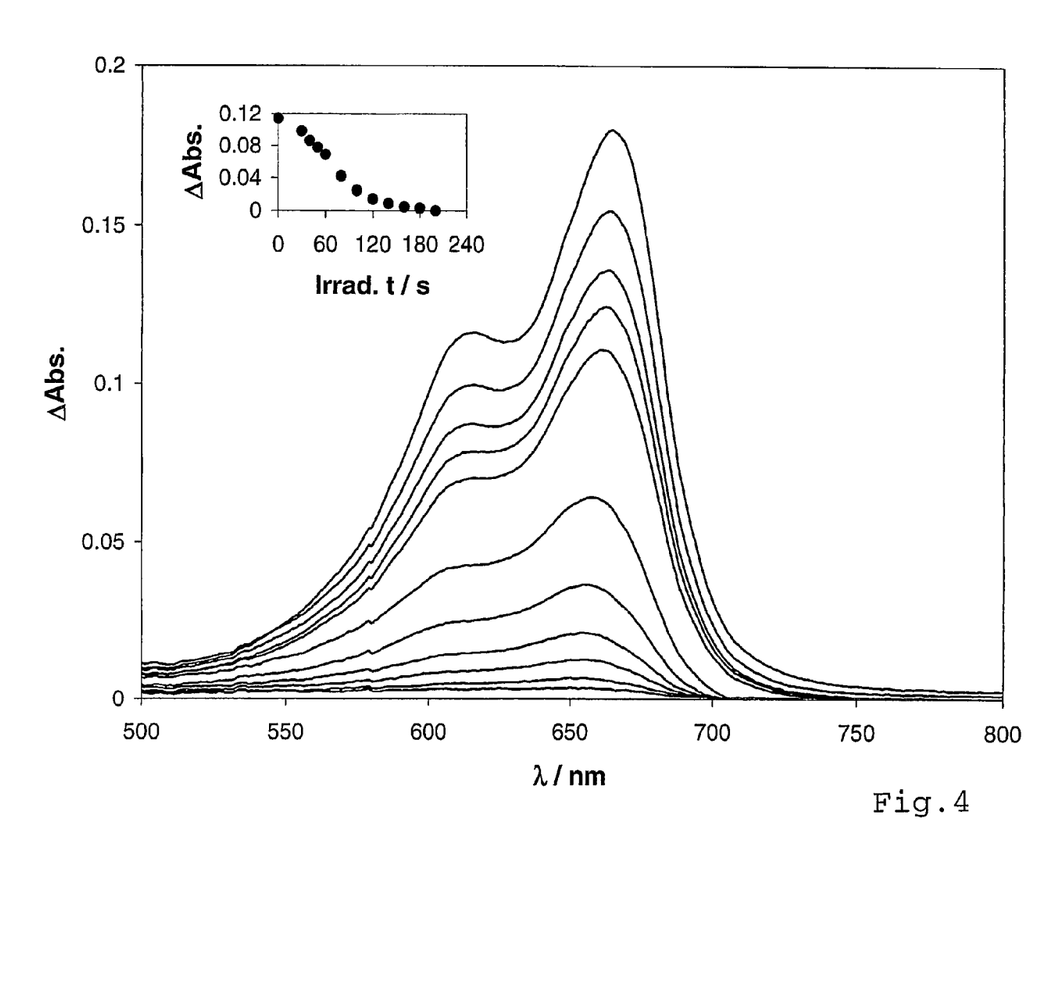
FIG. 4 relates to changes in UV/Visible absorption spectrum upon irradiation of methylene blue, $TiO_2$ and the sacrificial electron donor (SED) triethanolamine in hydroxyethyl cellulose with near UV light under anaerobic conditions.

Blank experiments carried out under anaerobic conditions using a film identical to Example 1 except with no semiconductor was present, showed no change in colour upon its subjection to a burst of near UV light (100 W blacklight bulb; 3 minutes). The latter experiment illustrates the essential role of the semiconductor in the near-UV irradiation activation step. In contrast, when a semiconductor material is present, as in Example 1, near UV irradiation under anaerobic conditions, leads to the rapid loss of colour as methylene blue is reduced to leuco-methylene blue by the TEOA present, photosensitized by the $TiO_2$ semiconductor material. The optical consequences of the near UV photoactivation step for Example 1 are illustrated in FIG. 4, which shows the observed change in its UV/Vis absorption spectrum with increasing time of irradiation with near UV light (100 W black light bulb). As the results illustrated in FIG. 4 show, with increasing irradiation time the absorbance spectral profile of methylene blue, i.e. MB decreases with increasing irradiation time under anaerobic conditions. The insert diagram illustrates the absorbance change due to methylene blue (measured at 610 nm) as a function of irradiation time using the data in the main diagram. Thus, after 3 min irradiation using the 100 W black-light bulb, under anaerobic conditions Example 1 is completely decolourised, i.e. activated.

Figure 5:
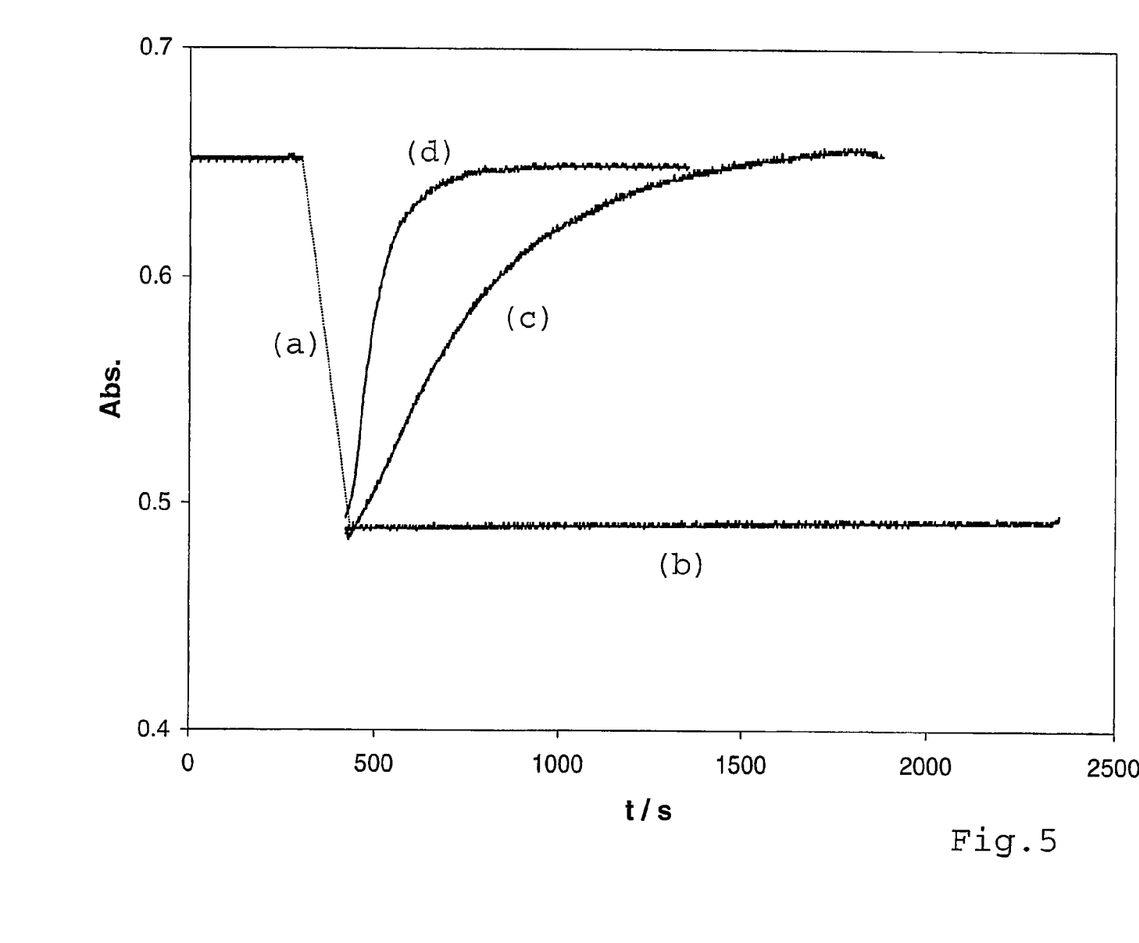
FIG. 5 relates to the observed variation in the absorbance at 610 nm of methylene blue, $TiO_2$ and the sacrificial electron donor (SED) triethanolamine in $TiO_2$ and hydroxyethyl cellulose upon exposure to near UV light and then storage under an anaerobic, aerobic and oxygen saturated atmosphere.

The reduced form of the redox-sensitive dye contained in the oxygen indicator is stable indefinitely under anaerobic conditions. But, upon exposure to air the original blue colour of the film is rapidly restored. This process is even faster if the film is exposed to pure oxygen, rather than air. These features are illustrated by the data in FIG. 5 which shows the observed variation in the absorbance (at 610 nm) of Example 1 upon (a) exposure to near UV light, which causes a rapid drop in absorbance corresponding to the bleaching of the MB photocatalysed by the $TiO_2$ particles, and subsequent storage under (b) an anaerobic (bottom line), (c) aerobic (middle line) and (d) oxygen saturated atmosphere.

Figure 6:
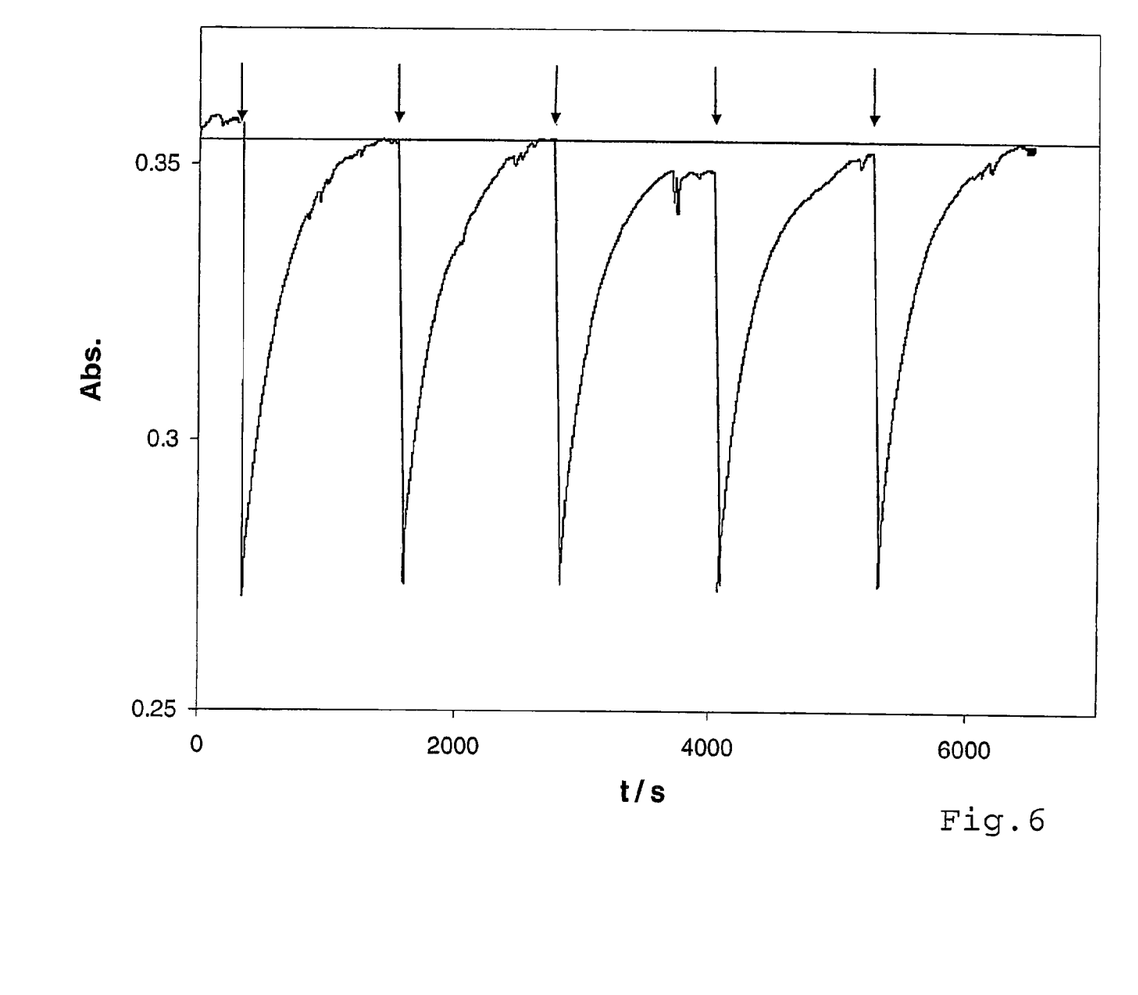
FIG. 6 relates to the observed variation in the absorbance at 610 nm of methylene blue, $TiO_2$ and the sacrificial electron donor (SED) triethanolamine in $TiO_2$ and hydroxyethyl cellulose in a repeated cycle of irradiation with near UV light under anaerobic conditions and then exposure to air.

The oxygen indicator is irreversible, in that it will only work once after activation with near UV light, provided the indicator is not exposed to another burst of near UV light. However, the oxygen indicator can be used over and over again in this format. Thus, FIG. 6 illustrates the observed variation in the absorbance (at 610 nm) of Example 1 in a repeated cycle of irradiation with near UV light under anaerobic conditions and exposure to air. From these results it can be seen that the oxygen indicator is irreversible but reusable.

A series of example oxygen indicators were prepared using, unless stated otherwise, an identical procedure to that reported above for Example 1, with only the nature, but not the amount, of redox-sensitive dye altered. Each of these films was tested for colour change response upon light activation in an anaerobic atmosphere. A measure of this response is the time taken for the absorbance change associated with the indicator at the wavelength of maximum absorbance of its most highly coloured (usually oxidised) form, to reach 50% of its maximum value, i.e. $t(response)_{50\%}$. The time taken for the photobleached films to recover 50% of their initial absorbance (i.e. $t(recovery)_{50\%}$) was also measured for these indicator films when exposed to oxygen. The latter is a measure of the sensitivity of these indicator films towards oxygen. The results of this work are summarised in Table 1.

TABLE 1 oxygen indicators using different redox-sensitive dyes

| Example | Oxygen Indicator | Colour Change | $t(response)_{50\%}$/ min | Colour change | $t(recovery)_{50\%}$/ min |
|---|---|---|---|---|---|
| 1 | MB/ TEOA/ $TiO_2$/HEC | B→W | <1 | W→B | <10 |
| 2 | DCIP/ TEOA/ $TiO_2$/HEC | B→W | <2 | W→B | <300 |
| 3 | RR/ TEOA/ $TiO_2$/HEC | V→W | <10 | W→V | <1 |
| 4 | IC/TEOA/ $TiO_2$/HEC | B→G* | <2 | G*→B | <5 |
| 5 | BV/ EDTA/ $TiO_2$/HEC | W→P | <2 | P→W | <1 |

Oxygen indicator: MB = methylene blue, DCIP = dichloroindophenol, RR = Resorufin, IC = indigo carmine; BV = benzyl viologen, TEOA = triethanol amine, $TiO_2$ = titanium (IV) oxide (Degussa P25) and HEC = hydroxyethyl cellulose.
Colour change: B = blue, W = white (i.e. colourless), V = violet, G* = green and luminescent and P = purple.

In Example 4 the reduced form of the indicator luminesces. Thus, the principles of operation of the oxygen indicator illustrated in FIG. 4 are not limited to colourimeric indicators, but also includes fluorimetric indicators. The latter comprises the same major components of the oxygen indicator but, instead of, or as well as, having a colourimetric redox sensitive dye, it contains a fluorimetric redox sensitive dye. In the case of the redox dye indigo carmine, the two dyes are the same species, i.e. indigo carmine acts both as a colourimetric and fluorimetric oxygen indicator. The latter is defined as a dyestuff that exhibits a different fluorescence for its reduced and oxidised forms. The latter is true of most fluorescent dyestuffs. Indigo carmine is a favoured fluorescent redox sensitive dye for use in the oxygen indicator.

In Example 5 a viologen indicator was used as the redox-sensitive dye. Unlike almost all reported oxygen indicators, Example 5 is colourless in the presence of oxygen and, after activation with near UV light, highly coloured in its absence. This oxygen indicator was prepared as follows: 0.05 g of P25 $TiO_2$, 0.05 g of benzylviologen (BV) and 0.05 g of the disodium salt of ethylenediamine tetraacetic acid (NaEDTA) were added to 2 g of a 5 wt % aqueous solution of HEC. The solution was thoroughly mixed and cast in the usual way.

The nature of the semiconductor (but not its concentration in the indicator formulation) used in the oxygen indicator was also varied from that used in Example 1 and characterised as described above. In this work all other experimental components and conditions were as used in the preparation of Example 1. The results of this work are as follows:

TABLE 2 oxygen indicators using different semiconductors

| Example | Oxygen Indicator | Colour change | $t(response)_{50\%}$/ min | Colour change | $t(recovery)_{50\%}$/ min |
|---|---|---|---|---|---|
| 1 | MB/ TEOA/ $TiO_2$/HEC | B→W | <1 | W→B | <10 |
| 6 | MB/ TEOA/ ZnO/HEC | B→W | <0.25 | W→B | <10 |

The nature of the polymer binder used the oxygen indicator was also varied from that used in Example 1 and characterised as described above. Example 7 used PMMA as the polymer binder and was prepared as follows: 0.05 g of P25 $TiO_2$, 0.01 g of MB and 0.1 g of triethanolamine were mixed with 2 g of a 5% solution of PMMA in chloromethane using a magnetic stirrer. This sensor ink preparation was then used to prepare an oxygen indicator in the usual way. Example 8 used PVP as the polymer binder and was prepared as follows: 0.05 g of P25 $TiO_2$, 0.01 g of MB and 0.1 g of triethanolamine were mixed with 2 g of a 5% solution of PVP in water using a magnetic stirrer. This sensor ink preparation was then used to prepare an oxygen indicator in the usual way. The films were then characterised as before and the results of this work are as follows:

TABLE 3 oxygen indicators using different polymers

| Example | Oxygen Indicator | Colour change | t(response)$_{50\%}$/ min | Colour change | t(recovery)$_{50\%}$/ min |
|---|---|---|---|---|---|
| 1 | MB/ TEOA/ TiO$_2$/HEC | B→W | <1 | W→B | <10 |
| 7 | MB/ TEOA/ TiO$_2$/ PMMA | B→W | <30 | W→B | <180 |
| 8 | MB/ TEOA/ TiO$_2$/PVP | B→W | <30 | W→B | <180 |

PMMA = polymethylmethacrylate and
PVP = polyvinylpyrolidone

For all oxygen indicators, a plasticiser, such as tributyl phosphate or dimethyl phthalate, can be added to the oxygen indicator formulation to improve oxygen diffusion through the film and, as a consequence lower markedly the indicator response and recovery times.

The nature of the sacrificial electron donor (but not its concentration in the indicator formulation) used in the oxygen indicator was also varied from that used in Example 1 and characterised as described above. In this work all other experimental components and conditions were as used in the preparation of Example 1. The results of this work are as follows:

TABLE 4 oxygen indicators using different sacrificial electron donors

| Example | Oxygen Indicator | Colour change | t(response)$_{50\%}$/ min | Colour change | t(recovery)$_{50\%}$/ min |
|---|---|---|---|---|---|
| 1 | MB/ TEOA/ TiO$_2$/HEC | B→W | <1 | W→B | <10 |
| 5 | BV/ EDTA/ TiO$_2$/HEC | W→P | <2 | P→W | <1 |
| 9 | MB/ Glycerol/ TiO$_2$/HEC | B→W | <2 | W→B | <10 |

The nature of the support substrate used in the oxygen indicator was also varied from that used in Example 1 and characterised as described above. In this work all other experimental components and conditions were as used in the preparation of Example 1. The results of this work are as follows:

TABLE 5 oxygen indicators using different substrate supports

| Example | Oxygen Indicator | Colour change | t(response)$_{50\%}$/ min | Colour change | t(recovery)$_{50\%}$/ min |
|---|---|---|---|---|---|
| 1 | MB/ TEOA/ TiO$_2$/ HEC/ Glass | B→W | <1 | W→B | <10 |
| 10 | MB/ TEOA/ TiO$_2$/ HEC/ aluminium foil | B→W | <1 | W→B | <10 |
| 11 | MB/ TEOA/ TiO$_2$/ HEC/ acetate plastic | B→W | <1 | W→B | <10 |

The indicator can also act as a detector for indicating exposure to light of about 200-400 nm. The greater the exposure to the light the greater the colour change. As the colour change is progressive, a graduated scale may be formed to indicate how much light the indicator has been exposed to. This feature is illustrated by the results in FIG. 8, for a typical film indicator, covered with a layer of Sellotape (Registered Trade Mark). The results show how the observed change in absorbance of the film at 610 nm is related to the total number of UV photos incident on the indicator film.

The indicator can also have a cover or be encapsulated in a medium which has a low oxidising agent permeability. This has the effect of slowing down the colour change of the indicator on exposure to an oxidisng agent, for example oxygen. This can therefore be used to indicate how long the indicator has been exposed to the oxidising agent by assessing the colour change. This feature is illustrated by the results in FIG. 7, for a typical film indicator covered with layers of different thickness of the largely oxygen impermeable polymer, PET. The results show that the thicker the covering film of PET, the larger the recovery time of the overall indicator film, after UV activation and subsequent exposure to air.

The invention claimed is:

1. An indicator for detecting an oxidising agent comprising:
    at least one redox sensitive material which displays different visible properties in the oxidized and reduced forms;
    at least one electron donor wherein the at least one electron donor is a mild reducing agent, and wherein the at least one electron donor is incapable of directly reducing the redox material; and
    at least one semiconductor material specifically sensitive to light of about 200-400 nm, the semiconductor material being selected from the group consisting of oxides of titanium, tin, tungsten, zinc, and mixtures thereof, wherein the redox sensitive material, electron donor, and semi-conductor material are in intimate contact with each other, and wherein upon irradiation of said semiconductor material by light of about 200-400 nm an electron is donated by the electron donor to the semiconductor material which in turn provides an electron to the redox sensitive material causing the redox sensitive material to become reduced, and wherein upon exposure to an oxidizing agent, the indicator irreversibly changes color.

2. An indicator according to claim 1 wherein the indicator is capable of detecting an oxidising agent in a gaseous state.

3. An indicator according to claim 1 wherein the indicator is capable of detecting the presence of oxygen.

4. An indicator according to claim 1 wherein the indicator is in the form of a tablet, pellet, plastic film.

5. An indicator according to claim 1 wherein the indicator comprises an ink that is printed onto a substrate in the form of a label, LOGO or text.

6. An indicator according to claim 1 wherein the redox sensitive material is a dye selected from the group consisting of a thiazine dyestuff, an oxazine dyestuff, an azine dyestuff, a triphenylmethane dyestuff, an indophenol dyestuff, an indigo dyestuff, viologen and mixtures thereof.

7. An indicator according to claim 1 wherein the electron donor is selected from any of an amine, a reducing saccharide, a readily oxidisable polymer, and an anti-oxidant.

8. An indicator according to claim 1 wherein the indicator comprises a binder for binding the redox sensitive material, electron donor material, and semi-conductor material in intimate contact with each other, said binder being selected from the group consisting of polymeric material of gelatin, hydroxyethyl cellulose (HEC), polyvinyl alcohol (PVA), ethyl cellulose (EC), cellulose acetate (CEA), polypyrolidone (PVP), polyethylene oxide, and polymethylmethacrylate (PMMA).

9. An indicator according to claim 1 wherein the indicator is attached to at least one inert material, selected from the group consisting of glass, paper, fabric, ceramic and metal.

10. An indicator according to claim 1 wherein the indicator is in the form of an ink.

11. An indicator according to claim 1 wherein the indicator comprises a cover having a very low oxidizing agent permeability which has the effect of preventing the color change of the UV-light activated indicator upon exposure to an oxidizing agent.

12. An indicator according to claim 11 wherein the cover comprises any of the following: PET, EVOH, PVDC or regenerated cellulose.

13. An indicator for indicating exposure to air using an oxidising agent comprising: at least one redox sensitive material which displays different visible properties in the oxidized and reduced forms;
at least one electron donor wherein the at least one electron donor is a mild reducing agent, and wherein the at least one electron donor is incapable of directly reducing the redox material; and
at least one semiconductor material specifically sensitive to light of about 200-400 nm, the semiconductor material being selected from the group consisting of oxides of titanium, tin, tungsten, zinc, and mixtures thereof,
wherein a color change in the indicator indicates exposure to light of about 200-400 nm.

14. An indicator according to claim 1 wherein the electron donor is selected from the group consisting of NaEDTA, TEOA, glucose, fructose, polyvinyl alcohol, ascorbic and citric acid.

15. An indicator for detecting an oxidising agent comprising:
at least one redox sensitive material which displays different visible properties in the oxidized and reduced forms;
at least one electron donor wherein the at least one electron donor is a mild reducing agent, and wherein the at least one electron donor is incapable of directly reducing the redox material; and
at least one semiconductor material specifically sensitive to light of about 200-400 nm, the semiconductor material being selected from the group consisting of oxides of tin, tungsten, zinc, and mixtures thereof, wherein the redox sensitive material, electron donor, and semi-conductor material are in intimate contact with each other, and wherein upon irradiation of said semiconductor material by light of about 200-400 nm an electron is donated by the electron donor to the semiconductor material which in turn provides an electron to the redox sensitive material causing the redox sensitive material to become reduced.

* * * * *